US 6,683,092 B1

(12) United States Patent
Tsang et al.

(10) Patent No.: US 6,683,092 B1
(45) Date of Patent: Jan. 27, 2004

(54) [3-($C_{5-14}$ALKYL-2-OXO-1,2,3,4-TETRAHYDRO-QUINOLIN-6-YL)-3-OXO-PROPENYL]-PHENYL AND [3-($C_{5-14}$ALKYL-2-OXO-1,2,3,4- TETRAHYDRO-QUINOLIN-6-YL)-3-OXO-PROPENYL]-HETEROARYL DERIVATIVES HAVING ANTI-TUMOR ACTIVITY

(75) Inventors: Kwok Yin Tsang, Irvine, CA (US); Santosh Sinha, Irvine, CA (US); Smita Bhat, Irvine, CA (US); Xiaoxia Liu, Tustin, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/410,219

(22) Filed: Apr. 9, 2003

(51) Int. Cl.[7] .................... A61K 31/47; A61K 31/4709; C07D 215/16; C07D 401/02
(52) U.S. Cl. .................. 514/312; 546/158; 544/238; 544/333; 544/405; 514/253; 514/256; 514/314
(58) Field of Search ................. 514/312, 314, 514/253, 256; 546/158; 544/238, 333, 405

(56) References Cited

U.S. PATENT DOCUMENTS

| | | | |
|---|---|---|---|
| 4,810,804 A | 3/1989 | Chandraratna | |
| 5,278,318 A | 1/1994 | Chandraratna | |
| 5,399,561 A | 3/1995 | Chandraratna | |
| 5,498,755 A | 3/1996 | Chandraratna et al. | |
| 5,556,996 A | 9/1996 | Beard et al. | |
| 5,602,130 A | 2/1997 | Chandraratna | |
| 5,616,712 A | * 4/1997 | Teng et al. | 546/158 |
| 5,672,710 A | 9/1997 | Beard et al. | |
| 5,677,323 A | 10/1997 | Chandraratna | |
| 5,739,338 A | 4/1998 | Beard et al. | |
| 5,780,647 A | 7/1998 | Vuligonda et al. | |
| 6,048,873 A | 4/2000 | Vasudevan et al. | |
| 6,124,455 A | 9/2000 | Teng et al. | |
| 6,127,382 A | 10/2000 | Beard et al. | |
| 6,147,224 A | 11/2000 | Vuligonda et al. | |
| 6,291,677 B1 | 9/2001 | Vasudevan et al. | |
| 6,344,463 B1 | 2/2002 | Chandrarantna | |
| 6,469,028 B1 | 10/2002 | Klein et al. | |
| 6,495,552 B2 | 12/2002 | Vasudevan et al. | |

OTHER PUBLICATIONS

Mangelsdorf et al. The Retinoid Recptors In: The Retinoids, edited by Sporn et al. pp. 319–349. (1994). Raven Press, Ltd., New York.
Dawson et al. Chemistry and Biology of Synthetic Retinoids. pp.: 324–356. (1990). CRC Press Inc.
Decroix et al., *J. Chem. Res. (S).* 4:134 (1978).
Dawson et al. *J. Med. Chem.* 29:1282 (1983).
Queguiner et al. *Bull Soc. Chimique de France.* No. 10 pages. 3678–3683 (1969).

* cited by examiner

Primary Examiner—Charanjit S. Aulakh
(74) *Attorney, Agent, or Firm*—Gabor L. Szekeres; Robert J. Baran; Martin A. Voet

(57) ABSTRACT

Compounds of the formula where the variables have the meaning defined in the specification have anti-tumor activity.

31 Claims, No Drawings

[3-($C_{5-14}$ALKYL-2-OXO-1,2,3,4-TETRAHYDRO-QUINOLIN-6-YL)-3-OXO-PROPENYL]-PHENYL AND [3-($C_{5-14}$ALKYL-2-OXO-1,2,3,4-TETRAHYDRO-QUINOLIN-6-YL)-3-OXO-PROPENYL]-HETEROARYL DERIVATIVES HAVING ANTI-TUMOR ACTIVITY

BACKGROUND OF THE INVENTION

1. Field of Invention

The present invention relates to [3-($C_{5-14}$ alkyl-2-oxo-1,2,3,4-tetrahydro-quinolin-6-yl)-3-oxo-propenyl]-phenyl and [3-($C_{5-14}$ alkyl-2-oxo-1,2,3,4-tetrahydro-quinolin-6-yl)-3-oxo-propenyl]-heteroaryl derivatives having anti-tumor activity. The present invention also relates to pharmaceutical compositions used for treating tumor bearing mammals in need of such treatment with the compounds of the invention, and particularly for treating mammals, including humans, suffering from breast and/or prostate cancer with the compounds of the invention.

2. Brief Description of Background Art

U.S. Pat. Nos. 6,495,552; 6,291,677; 6,344,463; 6,048,873; 6,124,455; 6,147,224; 5,672,710; 5,677,323; 5,739,338; 5,556,996; 5,602,130; 5,616,712; 5,278,318; 5,399,561; 5,498,755; 4,810,804; 5,739,338, 5,780,647, 6,127,382 and 6,469,028 disclose compounds which include a tetrahydroquinoline or dihydroquinoline nucleus. The compounds of these patents are generally considered to act as retinoids which are generally known and accepted in the art to be useful for treating animals of the mammalian species, including humans, for curing or alleviating the symptoms and conditions of numerous diseases and conditions. Generally speaking, among the conditions treatable with retinoids or like compounds are premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and Kaposi's sarcoma. Nevertheless, depending on the receptor sites through which they act and on other known and unknown factors, retinoid or like compounds can have different modes of action, particularly as anti-tumor activity is concerned.

For a general overview of the retinoid receptors see Mangelsdorf et al. (1994) The Retinoid Receptors In: The Retinoids, edited by Sporn et al. p 319–349. Raven Press, Ltd., New York. For another general overview see Dawson and William H. Okamura, Chemistry and Biology of Synthetic Retinoids, published by CRC Press Inc., 1990, pages 324–356.

The present invention is directed to certain N—$C_{5-11}$ alkyl and like "long chain" substituted tetrahydroquinolin-2-one derivatives, which surprisingly have significantly better anti-tumor activity than their analogs where the N is substituted with a shorter chain alkyl (or like) groups.

SUMMARY OF THE INVENTION

The present invention relates to compounds of Formula 1

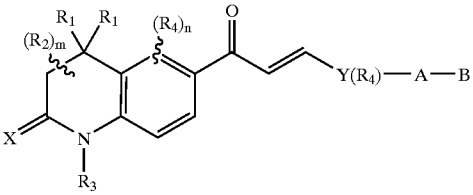

Formula 1 where X is O or S;
m is an integer having the values of 0 to 2;
n is an integer having the values of 0 to 3;
$R_1$ is independently H, or alkyl of 1 to 6 carbons;
$R_2$ is independently H, alkyl of 1 to 6 carbons, F, Cl, Br or I;
$R_3$ is alkyl of 5 to 11 carbons, alkenyl of 5 to 11 carbons and having one or two double bonds, alkynyl of 5 to 11 carbons and having one to two triple bonds, alkenyl-alkynyl having 5 to 11 carbons and one double and one triple bond, or
$R_3$ is $(CH_2)_r$-phenyl-$(CH_2)_s$—$(CH_3)_t$ where r is an integer having the values of 0 to 7, s is an integer having the values of 0 to 6, and t is an integer having the values of 0 to 1, with the provisos that the sum of r, s and t is in the range of 1 to 7, the phenyl group is 1,3 (meta) or 1,4 (para) substituted with the $(CH_2)_r$ and $(CH_2)_s$—$(CH_3)_t$ groups, the phenyl group optionally being further substituted with one or two $R_4$ groups;
$R_4$ is independently H, alkyl of 1 to 6 carbons, F, Cl, Br or I, alkoxy of 1 to 3 carbons, thioalkoxy of 1 to 3 carbons; $NO_2$, amino, alkylamino or dialkylamino where the alkyl group has 1 to 3 carbons;
Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_4$ groups;
A is $(CH_2)_q$ where q is 0–5, branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and
B is COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-$C_{1-6}$ alkylsilyl, where $R_7$ is an alkyl, cycloalkyl or alkenyl group containing 1 to 5 carbons, $R_8$ is an alkyl group of 1 to 10 carbons, $OCH_2O_{C-1-3}$ alkyl or $OCH_2OCO_{C-1-3}$ alkyl, or trimethylsilylalkyl where the alkyl group has 1 to 10 carbons, or a cycloalkyl group of 5 to 10 carbons, or $R_8$ is phenyl or $C_{1-6}$ alkylphenyl, $R_9$ and $R_{10}$ independently are hydrogen, an alkyl group of 1 to 10 carbons, or a cycloalkyl group of 5–10 carbons, or phenyl or $C_{1-6}$ alkylphenyl, $R_{11}$ is $C_{1-6}$ alkyl, phenyl or $C_{1-6}$ alkylphenyl, $R_{12}$ is $C_{1-6}$ alkyl, and $R_{13}$ is divalent alkyl radical of 2–5 carbons, or a pharmaceutically acceptable salt of said compound.

The present invention also relates to pharmaceutical compositions incorporating the compounds of Formula 1 and to methods of treatment of tumor bearing mammals with pharmaceutical compositions containing one or more compounds of Formula 1, and particularly to methods of treating breast cancer and prostate cancer with compounds of the invention.

DETAILED DESCRIPTION OF THE INVENTION

GENERAL EMBODIMENTS AND SYNTHETIC METHODOLOGY

Definitions

The term alkyl refers to and covers any and all groups which are known as normal alkyl and branched-chain alkyl.

A pharmaceutically acceptable salt may be prepared for any compound in this invention having a functionality capable of forming a salt, for example an acid functionality. A pharmaceutically acceptable salt is any salt that retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The compounds of the present invention include at least one olephinic double bonds about which trans and cis (E and Z) stereoisomerism can exist. Unless specifically indicated by formula or chemical name the compounds of the present invention, including the preferred embodiments can have both the trans and cis (E and Z) orientations of substituents relative to the double bond or bonds. Some of the compounds of the present invention may contain one or more chiral centers and therefore may exist in enantiomeric and diastereomeric forms. The scope of the present invention is intended to cover the trans and cis (E and Z) isomers as specifically shown and/or named, as well as pure enantiomers (optical isomers), diastereomers, mixtures of diastereomers and racemic mixtures of enantiomers.

Reaction Scheme 1 discloses a presently preferred synthetic route to compounds of the invention. In accordance with Reaction Scheme 1 a 4-bromo-aniline derivative of Formula 2 is reacted with an acryloyl chloride derivative of Formula 3 in an aprotic neutral solvent in the presence of an acid acceptor, such as triethyl amine (TEA), to provide the phenyl amide derivative of Formula 4. The aniline derivative of Formula 2 is already substituted with the $R_4$ groups, (the variables $R_4$ and n are defined as in connection with Formula 1) although the 4-bromo aniline used for the preparation of the presently preferred compounds of the invention is unsubstituted (n=0). The substitituted anilines of Formula 2 are either available commercially, or can be prepared in accordance with the chemical scientific and patent literature, or by such modifications of known synthetic procedures that are readily apparent to those skilled in the art.

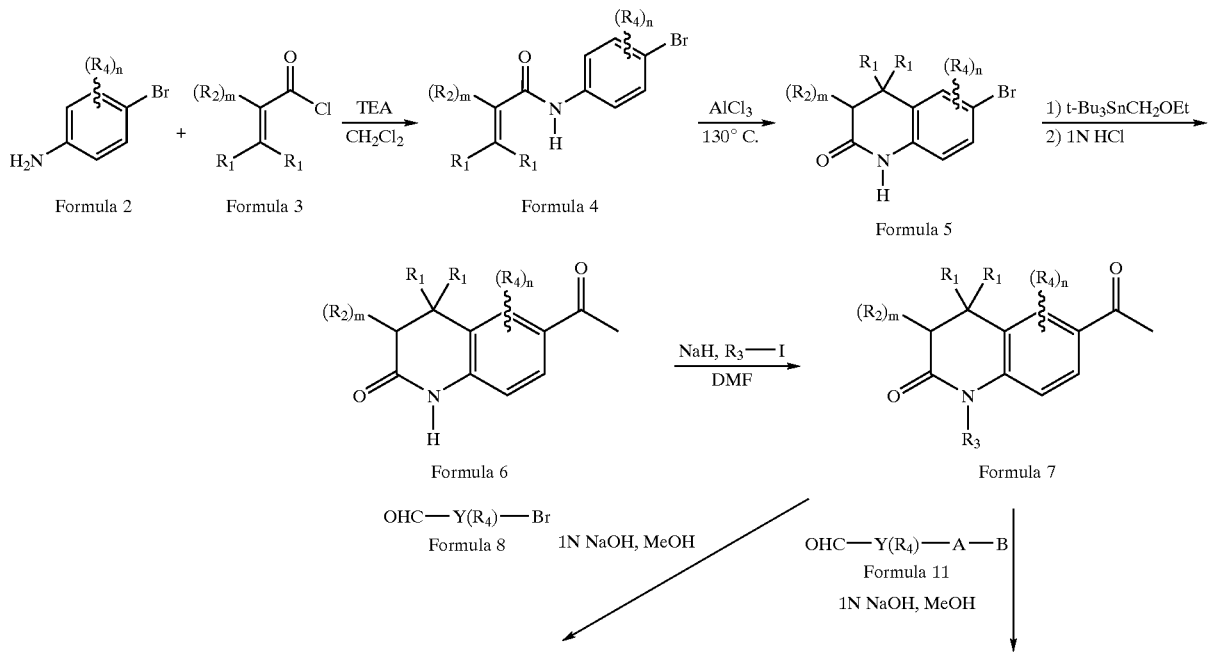

Reaction Scheme 1

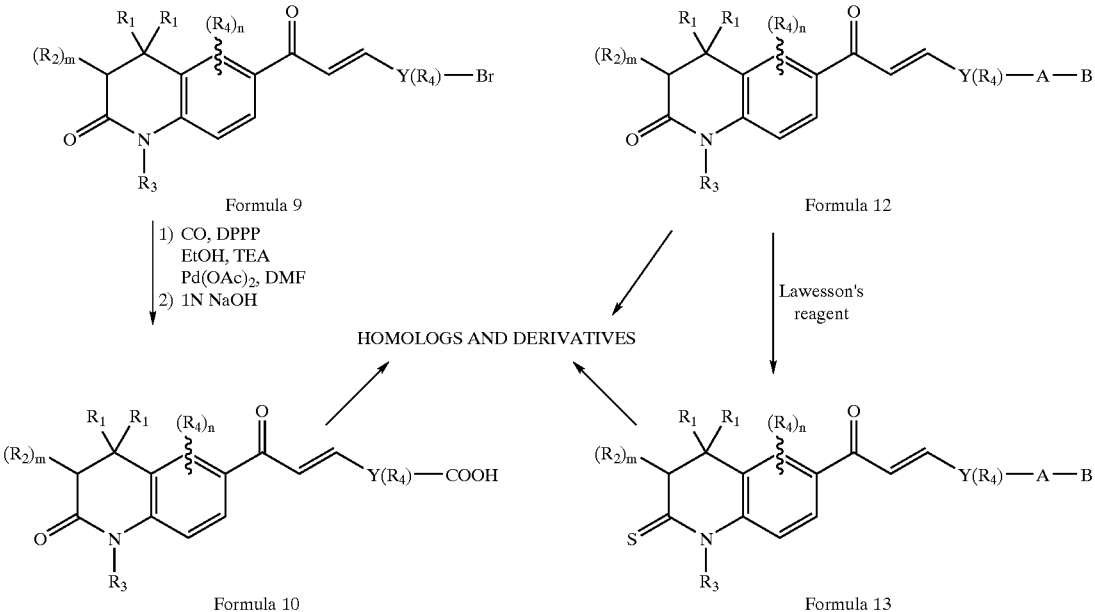

Formula 9

1) CO, DPPP
   EtOH, TEA
   Pd(OAc)₂, DMF
2) 1N NaOH

Formula 12

Lawesson's reagent

HOMOLOGS AND DERIVATIVES

Formula 10

Formula 13

In the formula (Formula 3) of the acryloyl chloride derivative the variables R₁, R₂ and m are defined as in connection with Formula 1. An example of the acryloyl chloride derivative of Formula 3 that is used for the synthesis of the presently preferred compounds of the invention is commercially available 3,3-dimethylacryloyl chloride (R₁ is methyl and m=0). Acrylic acid derivatives of Formula 3 can also be obtained, generally speaking, in accordance with the chemical scientific and patent literature, or by such modifications of known synthetic procedures that are readily apparent to those skilled in the art. The acrylic acid amide derivative of Formula 4 is cyclized under Friedel Crafts conditions to provide the 3,4-dihydro-1H-quinolin-2-one derivative of Formula 5.

The 3,4-dihydro-1H-quinolin-2-one derivative of Formula 5 is reacted with tributyl(1-ethoxyvinyl)tin to introduce an acetyl group into the 6 position of the quinoline nucleus and to provide a 6-acetyl-3,4-dihydro-1H-quinolin-2-one derivative of Formula 6. The R₃ group (R₃ is as defined in connection with Formula 1) is introduced into the molecule by treatment of the compound of Formula 6 with a reagent of the formula R₃—I and a strong base, such as sodium hydride in a polar aprotic solvent, such as dimnethylformamide (DMF). Instead of the iodo derivative R₃—I, other alkylating agents of the formula R₃—X₁ (where X₁ is a leaving group) could also be used in this reaction to provide a 6-acetyl-1-alkyl (or 1-phenylalkyl) 3,4-dihydro-1H-quinolin-2-one derivative of Formula 7. The 6-acetyl-1-alkyl (or 1-phenylalkyl) 3,4-dihydro-1H-quinolin-2-one derivative of Formula 7 is reacted with a bromophenyl or bromo heteroaryl aldehyde of Formula 8 to give the 1-alkyl-6-[3-(bromo phenyl or bromo-heteroaryl)-acryloyl]-3,4-dihydro-1H-quinolin-2-one of Formula 9. The bromo compound of Formula 9 is reacted with carbon monoxide in the presence of 1,3-bis(diphenylphosphino)propane (DPPP), palladium acetate (Pd(OAc)₂), triethylamine (TEA) in dimethylformamide and ethanol and thereafter with base (such as NaOH or KOH) to provide [3-(1-alkyl-2-oxo-1,2,3,4-tetrahydro-quinolin-6-yl)-3-oxo-propenyl]-benzoic or heteroaryl carboxylic acids of Formula 10.

Alternatively, the 6-acetyl-1-alkyl (or 1-phenylalkyl) 3,4-dihydro-1H-quinolin-2-one derivative of Formula 7 is reacted with an aldehyde of Formula 11 to provide [3-(1-alkyl-2-oxo-1,2,3,4-tetrahydro-quinolin-6-yl)-3-oxo-propenyl]-benzoic or heteroaryl compounds of Formula 12.

In the formulas of the reagents of Formula 8 and Formula 11 the variables Y(R₄) and A—B are defined as in connection with Formula 1. The reagents of Formula 8 are bromo substituted benzaldehydes, bromo substituted naphthylaldehydes or bromo substituted heteroaryl aldehydes which, generally speaking, can be obtained in accordance with the chemical scientific and patent literature, or by such modifications of known synthetic procedures that are readily apparent to those skilled in the art. An example for the reagent of Formula 8 that is used for the synthesis of one or more preferred compounds of the invention is 4-bromobenzaldehyde. Other examples are 3-bromobenzaldehyde, 5-bromo-pyridine-2-aldehyde, 4-bromo-pyridine-2-aldehyde, 4-bromo-thiophene-2-aldehyde, 5-bromo-thiophene-2-aldehyde, 4-bromo-furan-2-aldehyde, and 5-bromo-furan-2-aldehyde.

In the preparation of several preferred exemplary compounds of the invention the reagent of Formula 11 is 4-carboxybenzaldehyde. Examples of other reagents within the scope of Formula 11 are: 5-carboxy-pyridine-2-aldehyde, 4-carboxy-pyridine-2-aldehyde, 4-carboxy-thiophene-2-aldehyde, 5-carboxy-thiophene-2-aldehyde, 4-carboxy-furan-2-aldehyde and 5-carboxy-furan-2-aldehyde. These compounds are available in accordance with the chemical literature; see for example Decroix et al., *J. Chem. Res.*(S), 4: 134 (1978); Dawson et al., *J. Med. Chem.* 29:1282 (1983); and Queguiner et al., *Bull Soc. Chimique de France* No. 10, pp. 3678–3683 (1969). The condensation reaction between the compounds of Formula 7 and Formula 8 or between the compounds of Formula 7 and Formula 11 is conducted in the presence of base in an alcoholic solvent. Preferably, the reaction is conducted in methanol in the presence of sodium hydroxide. Those skilled in the art will recognize this condensation reaction as an aldol condensation, and in case of the herein described preferred examples (condensing a ketone of Formula 7 with an aldehyde of Formula 8 or of Formula 11) as a Claisen-Schmidt reaction. (See March: *Advanced Organic Chemis-* try: *Reactions, Mechanisms, and Structure*, pp. 694–695 McGraw Hill (1968).

The [3-(1-alkyl-2-oxo-1,2,3,4-tetrahydro-quinolin-6-yl)-3-oxo-propenyl]-benzoic or heteroaryl compounds of Formula 12 can be converted to the corresponding 2-thio analogs of Formula 13 by treatment with [2,4-bis(4-methoxyphenyl)-1,3-dithia-2,4-diphosphatane-2,4-disulfide. (Lawesson's reagent). The compounds of Formulas 10, 12 and 13 are within the scope of Formula 1 and within the scope of the present invention. Those of skilled in the art will readily recognize that several synthetic transformations can be performed on the compounds of Formulas 10, 12 and 13 to obtain other compounds which are still in the scope of the invention, keeping the scope of the A—B group in mind. Esterification and/or saponification, homologation, formation of carboxylic acid amides, and reduction of carboxylic acid or ester group to the aldehyde or the primary alcohol level serving as examples. These reactions per se are well known in the art and can be readily performed by those skilled in the art to obtain "homologs and derivatives" which are still within the scope of the invention and wherein the A—B group has the scope defined in connection with Formula 1.

SPECIFIC EMBODIMENTS OF THE COMPOUNDS OF THE INVENTION

Referring now to Formula 1, in the preferred compounds of the invention the variable $R_1$ represents alkyl groups of 1 to 3 carbons, and even more preferably methyl. Still more preferably the 1,2,3,4-tetrahydroquinoline group is substituted in the 4 position by geminal dimethyl groups, and still further substitution of the non-aromatic portion by additional $R_2$ groups is presently not preferred. The $R_3$ group of the preferred compounds is alkyl of 5 to 11 carbons, or phenylalkyl, even more preferably alkyl of 6 to 9 carbons, or phenylethyl. The X group of the presently preferred compounds is oxygen. Preferred $R_4$ groups are alkyl of 1 to 3 carbons, F, Cl, Br, I, or alkoxy of 1 to 3 carbons. Even more preferably the aromatic portion of the tetrahydroquinoline nucleus is substituted only in the 6 position by the 3-oxo-propenyl-phenyl or by the 3-oxo-propenyl-heteroaryl group (the variable n in Formula 1 is zero).

In the presently preferred compounds of the invention the Y group is phenyl and there is no optional $R_4$ substituent. Compounds are also preferred where the Y group is pyridyl, thienyl or furyl. Preferred A—B groups are $(CH_2)_q$—COOH, $(CH_2)_q$—COOR$_8$, and $(CH_2)_q$—CONR$_9$R$_{10}$ and preferably q is zero. Even more preferably the A—B group is COOH or COOR$_8$ where $R_8$ is preferably alkyl of 1 to 3 carbons, $OCH_2O_{C-1-3}$ alkyl or $OCH_2OCO_{C-1-3}$ alkyl. The phenyl group is preferably 1,4 (para) substituted by the 3-oxo-propenyl and A—B groups. When the Y group is pyridyl, it is preferably 1,5-substituted by the 3-oxo-propenyl and A—B groups.

The synthesis of the presently most preferred compounds of the invention is shown in Reaction Scheme 2 and a detailed description of the experimental procedures for synthesizing these most preferred exemplary compounds is also provided below.

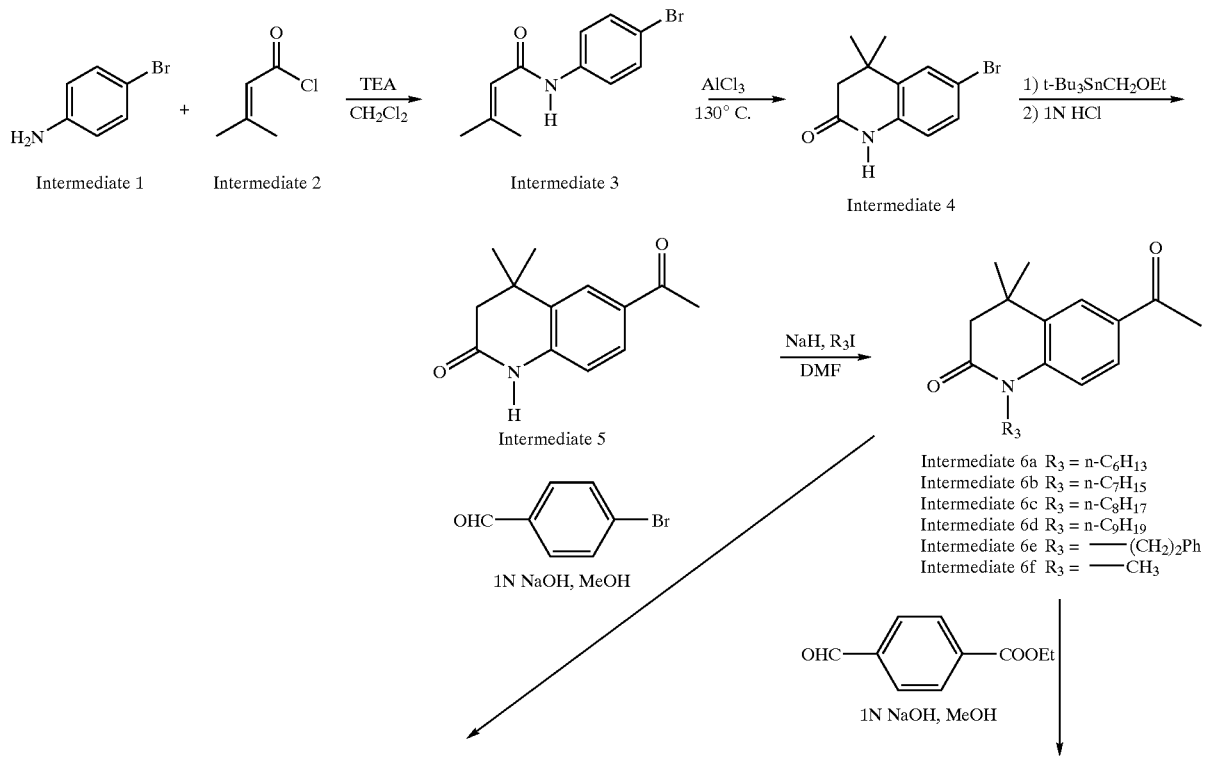

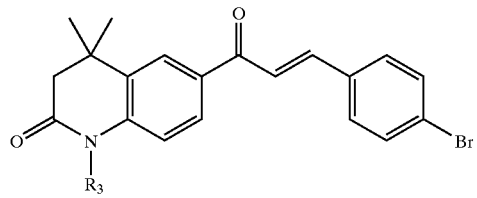
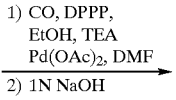
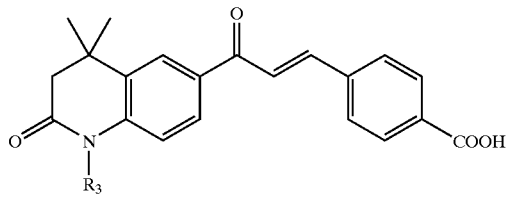

Intermediate 7d R₃ = n-C₉H₁₉
Intermediate 7e R₃ = ——(CH₂)₂Ph
Intermediate 7f R₃ = CH₃

Compound 8a R₃ = n-C₆H₁₃
Compound 8b R₃ = n-C₇H₁₅
Compound 8c R₃ = n-C₈H₁₇
Compound 8d R₃ = n-C₉H₁₉
Compound 8e R₃ = ——(CH₂)₂Ph
Compound 8f R₃ = CH₃

N-(4-Bromophenyl)-3-methylbut-2-enoic Amide (Intermediate 3)

3,3-Dimethylacryloyl chloride (Intermediate 1, 4.16 g, 35.1 mmol) was slowly added to a solution of 4-bromoaniline (Intermediate 2, 5.00 g, 29.2 mmol) in 25 mL of methylene chloride. After stirring at room temperature for 20 min, triethylamine (2.5 mL) was added dropwise to the mixture. The resulting solution was stirred at room temperature for 3 h and then poured on 100 mL of ice-water mixture. The organic layer was separated, washed with brine (2×20 mL), dried (MgSO₄) and concentrated at reduced pressure to give a yellow residue. Purification by flash chromatography (90:10 hexane/ethyl acetate) afforded the title compound as a yellow solid (7.43 g, 100% yield).

$^1$H NMR (CDCl₃, 300 MHz) δ 7.34 (s, 4H), 7.1 (bs, 1H), 5.69 (s, 1H), 2.23 (s, 3H), 1.91 (s, 3H).

6-Bromo-4,4-dimethyl-3,4-dihydro-1H-quinolin-2-one (Intermediate 4)

Aluminum chloride (5 g, 37.5 mmol) was added portionwise into N-(4-bromophenyl)-3-methylbut-2-enoic amide (Intermediate 3, 7.69 g, 30.0 mmol) in a 500 mL beaker at 130° C. over 1 h. The beaker was then cooled to 80° C. and another portion of aluminum chloride (1 g, 7.5 mmol) was added. After stirring at 80° C. for 0.5 h, the beaker was cooled with an ice-bath and ice was added slowly into the mixture. The resulting slurry was then extracted with ether (3×10 mL). The combined organic layer was washed with brine (1×10 mL), saturated NaHCO₃ (1×10 mL), dried (MgSO₄) and concentrated at reduced pressure. Purification by flash chomatography (75:25 hexane/ethyl acetate) yielded the title compound as a pale yellow solid (5.20 g, 68% yield).

$^1$H NMR (CDCl₃, 300 MHz) δ 7.40 (d, J=2.4 Hz, 1H), 7.27–7.31 (m, 2H), 6.65 (bs, 1H), 2.47 (s, 2H), 1.32 (s, 6H).

6-Acetyl-4,4-dimethyl-3,4-dihydro-1H-quinolin-2-one (Intermediate 5)

A solution of 6-bromo-4,4-dimethyl-3,4-dihydro-1H-quinolin-2-one (Intermediate 4, 270 mg, 1.06 mmol) in 5 ml of THF was first degassed by bubbling with argon for 30 min. Tributyl(1-ethoxyvinyl)tin (766 mg, 2.12 mmol) and PdCl₂(PPh₃)₂ (37mg, 0.05 mmol) were added. After stirring at 80° C. for 18 h, the mixture was cooled to room temperature and 3 mL of 10% HCl was added. The mixture was then stirred for another 30 min before extracted with ethyl acetate (3×10 mL). The combined organic layer was washed with brine (1×10 mL), dried (MgSO₄) and concentrated at reduced pressure. Purification by flash chromatography (50:50 hexane/ethyl acetate) yielded the title compound as a white solid (154 mg, 67% yield).

$^1$H NMR (CDCl₃, 300 MHz) δ 9.10 (bs, 1H), 7.95 (d, J=1.8 Hz, 1H), 7.80 (dd, J=1.8, 8.1 Hz, 1H), 6.89 (d, J=8.1 Hz, 1H), 2.59 (s, 3H), 2.54 (s, 2H), 1.38 (s, 6H).

N-Hexyl-6-acetyl-4,4-dimethyl-3,4-dihydro-1H-quinolin-2-one (Intermediate 6a)

Sodium hydride (21 mg, 90 mmol) was slowly added into a solution of 6-acetyl-4,4-dimethyl-3,4-dihydro-1H-quinolin-2-one (Intermediate 5, 98 mg, 45 mmol) in 3 mL of DMF at 0° C. After stirring at 0° C. for 10 min, 1-iodo-n-hexane (29 mg, 135 mmol) was added to the reaction mixture and the ice-bath was removed. The reaction was allowed to stir for 2 h before quenching with ice water. The resulting solution was then extracted with ether (3×10 mL), washed with brine (1×10 mL), dried (MgSO₄) and concentrated at reduced pressure. Purification by flash chromatography (75:25 hexane/ethyl acetate) yielded the title compound as a colorless oil (41.8 mg, 31% yield).

$^1$H NMR (CDCl₃, 300 MHz) δ 7.93 (d, J=2.1 Hz, 1H), 7.86 (dd, J=2.1, 8.4 Hz, 1H), 7.06 (d, J=8.4 Hz, 1H), 3.96–4.01 (m, 2H), 2.59 (s, 3H), 2.53 (s, 2H), 1.58–1.66 (m, 3H), 1.29–1.41 (m, 11H), 0.86–0.91 (m, 3H).

N-Heptyl-6-acetyl-4,4-dimethyl-3,4-dihydro-1H-quinolin-2-one (Intermediate 6b)

Following a procedure similar to that used for the preparation of Intermediate 6a but using 1-iodo-n-heptane as the alkylating reagent the title compound was obtained as a colorless oil (66% yield).

$^1$H NMR (CDCl₃, 300 MHz) δ 7.93 (d, J=2.1 Hz, 1H), 7.86 (dd, J=2.1, 8.4 Hz, 1H), 7.06 (d, J=8.4 Hz, 1H), 3.96–4.01 (m, 2H), 2.59 (s, 3H), 2.53 (s, 2H), 1.59–1.66 (m, 3H), 1.24–1.39 (m, 13H), 0.86–0.90 (m, 3H).

N-Octyl-6-acetyl-4,4-dimethyl-3,4-dihydro-1H-quinolin-2-one (Intermediate 6c)

Following a procedure similar to that used for the preparation of Intermediate 6a but using 1-iodo-n-octane as the alkylating reagent the title compound was obtained as a colorless oil (86% yield).

$^1$HNR (CDCl₃, 300 MHz) δ 7.93 (d, J=2.1 Hz, 1H), 7.86 (dd, J=2.1, 8.4 Hz, 1H), 7.05 (d, J=8.4 Hz, 1H), 3.96–4.01 (m, 2H), 2.59 (s, 3H), 2.53 (s, 2H), 1.57–1.63 (m, 3H), 1.27–1.33 (m, 15H), 0.86–0.90 (m, 3H).

N-Nonyl-6-acetyl-4,4-dimethyl-3,4-dihydro-1H-quinolin-2-one (Intermediate 6d)

Following a procedure similar to that used for the preparation of Intermediate 6a but using 1-iodo-n-nonane as the alkylating reagent the title compound was obtained as a colorless oil (70% yield).

$^1$H NMR (CDCl$_3$, 300 MHz) δ 7.86 (d, J=2.1 Hz, 1H), 7.86 (dd, J=2.1, 8.4 Hz, 1H), 6.99 (d, J=8.4 Hz, 1H), 3.89–3.94 (m, 2H), 2.52 (s, 3H), 2.45 (s, 2H), 1.54–1.65 (m, 3H), 1.19–1.32 (m, 17H), 0.78–0.82 (m, 3H).

N-Phenylethyl-6-acetyl-4,4-dimethyl-3,4-dihydro-1H-quinolin-2-one (Intermediate 6e)

Following a procedure similar to that used for the preparation of Intermediate 6a but using (2-iodo-ethyl)benzene as the alkylating reagent the title compounds was obtained as a colorless oil (34% yield).

$^1$H NMR (CDCl$_3$, 300 MHz) δ 7.94 (d, J=1.5 Hz, 1H), 7.86 (dd, J=1.5, 5.4 Hz, 1H), 7.23–7.31 (m, 5H), 7.09 (d, J=5.4 Hz, 1H), 4.23–4.26 (m, 2H), 2.94–2.97 (m, 2H), 2.60 (s, 3H), 2.52 (s, 2H), 1.34 (s, 6H).

N-Methyl-6-acetyl-4,4-dimethyl-3,4-dihydro-1H-guinolin-2-one (Intermediate 6f)

Following a procedure similar to that used for the preparation of Intermediate 6a but using iodomethane as the alkylating reagent the title compound was obtained as a colorless oil (32% yield).

$^1$H NMR (CDCl$_3$, 300 MHz) δ 7.94 (d, J=2.1 Hz, 1H), 7.86 (dd, J=2.1, 8.4 Hz, 1H), 7.05 (d, J=8.4 Hz, 1H), 3.43 (s, 3H), 2.60 (s, 3H), 2.55 (s, 2H), 1.34 (s, 6H).

6-[3-(4-Bromophenyl)acryloyl]-4,4-dimethyl-1-nonyl-3,4-dihydro-1H-guinolin-2-one (Intermediate 7d)

4-Bromobenzaldehyde (47 mg, 25.9 mmol) was added to a solution of N-nonyl-6-acetyl-4,4-dimethyl-3,4-dihydro-1H-quinolin-2-one (Intermediate 6d, 89 mg, 25.9 mmol) in 2 mL of 1 N NaOH and 4 mL of methanol. After stirring at room temperature for 18 h, the reaction mixture was extracted with ethyl acetate (3×10 mL). The combined organic layer was washed with brine (1×10 mL), dried (MgSO$_4$) and concentrated at reduced pressure. Purification by flash chomatography (90:10 hexane/ethyl acetate) gave the title compound as a yellow oil (68 mg, 52% yield).

$^1$H NMR (CDCl$_3$, 300 MHz) δ 8.01 (d, J=1.8 Hz, 1H), 7.84 (dd, J=1.8, 8.7 Hz, 1H), 7.76 (d, J=15.9 Hz, 1H), 7.26–7.58 (m, 5H), 7.10 (d, J=8.7 Hz, 1H), 3.98–4.03 (m, 2H), 2.55 (s, 2H), 1.59–1.65 (m, 3H), 1.27–1.36 (m, 17H), 0.86–0.90 (m, 3H).

6-[3-(4-Bromophenyl)acryloyl]-4,4-dimethyl-1-phenylethyl-3,4-dihydro-1H-quinolin-2-one (Intermediate 7e)

Following a procedure similar to that used for the preparation of Intermediate 7d but using N-phenylethyl-6-acetyl-4,4-dimethyl-3,4-dihydro-1H-quinolin-2-one (Intermediate 6e) as the starting material afforded the title compound as a light yellow oil (77% yield).

$^1$H NMR (CDCl$_3$, 300 MHz) δ 8.02 (d, J=2.1 Hz, 1H), 7.95 (dd, J=2.1, 8.4 Hz, 1H), 7.77 (d, J=15.6 Hz, 1H), 7.51–7.59 (m, 5H), 7.24–7.32 (m, 5), 7.14 (d, J=8.4 Hz, 1H), 4.27–4.29 (m, 2H), 2.95–3.00 (m, 2H), 2.55 (s, 2H), 1.31 (s, 6H).

6-[3-(4-Bromophenyl)acryloyl]-4,4-dimethyl-1-methyl-3,4-dihydro-1H-quinolin-2-one (Intermediate 7f)

Following a procedure similar to that used for the preparation of Intermediate 7d but using N-methyl-6-acetyl-4,4-dimethyl-3,4-dihydro-1H-quinolin-2-one (Intermediate 6f) as the starting material afforded the title compound as a light yellow oil (51% yield).

$^1$H NMR (CDCl$_3$, 300 MHz) δ 8.01 (d, J=1.8 Hz, 1H), 7.95 (dd, J=1.8, 8.4 Hz, 1H), 7.76 (d, J=15.6 Hz, 1H), 7.50–7.79 (m, 5H), 7.09 (d, J=8.4 Hz, 1H), 3.45 (s, 3H), 2.57 (s, 2H), 1.37 (s, 6H).

4-[3-(1-Hexyl-4,4-dimethyl-2-oxo-1,2,3,4-tetrahydro-quinolin-6-yl)-3-oxo-propenyl]-benzoic acid (Compound 8a)

Methyl 4-formylbenzoate (22 mg, 13.4 mmol) was added to a solution of N-hexyl-6-acetyl 4,4-dimethyl-3,4-dihydro-1H-quinolin-2-one (Intermediate 6a, 40 mg, 13.3 mmol) in 2 mL of 1 N NaOH and 4 mL of methanol. After stirring at room temperature for 18 h, the reaction mixture was extracted with ethyl acetate (3×10 mL). The combined organic layer was washed with brine (1×10 mL), dried (MgSO$_4$) and concentrated at reduced pressure. Purification by flash chormatography (50:49:1 hexane/ethyl acetate/acetic acid) gave the title compound as a light yellow solid (18.9 mg, 33% yield).

$^1$H NMR (acetone-d$_6$, 300 MHz) δ 11.32 (bs, 1H), 7.81–8.17 (m, 8H), 7.33 (d, J=9.3 Hz, 1H), 4.03–4.08 (m, 2H), 2.54 (s, 2H), 1.62–1.65 (m, 2H), 1.26–1.45 (m, 12H), 0.88–0.91 (m, 3H).

4-[3-(1-Heptyl-4,4-dimethyl-2-oxo-1,2,3,4-tetrahydro-quinolin-6-yl)-3-oxo-propenyl]-benzoic acid (Compound 8b)

Following a procedure similar to that used for the preparation of Compound 8a but using N-heptyl-6-acetyl-4,4-dimethyl-3,4-dihydro-1H-quinolin-2-one (Intermediate 6b) as the starting material afforded the title compound as a light yellow solid (51% yield).

$^1$H NM (acetone-d$_6$, 300 MHz) δ 11.35 (bs, 1H), 7.80–8.16 (m, 8H), 7.32 (d, J=9.0 Hz, 1H), 4.02–4.07 (m, 2H), 2.53 (s, 2H), 1.55–1.64 (m, 2H), 1.24–1.43 (m, 14H), 0.84–0.89 (m, 3H).

4-[3-(1-Octyl-4,4-dimethyl-2-oxo-1,2,3,4-tetrahydro-quinolin-6-yl)-3-oxo-propenyl]-benzoic acid (Compound 8c)

Following a procedure similar to that used for the preparation of Compound 8a but using N-octyl-6-acetyl-4,4-dimethyl-3,4-dihydro-1H-quinolin-2-one (Intermediate 6c) as starting material afforded the title compound as a light yellow solid (24% yield).

$^1$H NMR (acetone-d$_6$, 300 MHz) δ 11.32 (bs, 1H), 7.80–8.16 (m, 8H), 7.32 (d, J=9.0 Hz, 1H), 4.02–4.07 (m, 2H), 2.53 (s, 2H), 1.55–1.64 (m, 2H), 1.25–1.44 (m, 16H), 0.84–0.87 (m, 3H).

4-[3-(1-Nonyl-4,4-dimethyl-2-oxo-1,2,3,4-tetrahydro-quinolin-6-yl)-3-oxo-propenyl]-benzoic acid (Compound 8d)

A solution of 6-[3-(4-bromophenyl)acryloyl]-4,4-dimethyl-1-nonyl-3,4-dihydro-1H-quinolin-2-one (Intermediate 7d, 68 mg, 0.13 mmol), 1,3-bis(diphenylphosphino)propane (20 mg, 0.05 mmol) and palladium acetate (11 mg, 0.05 mmol) in 5 mL of dimethylformamide in a sealed tube was added 1 mL of triethylamine and 2 mL of anhydrous ethanol. Carbon monoxide was bubbled through the solution for 20 min, then the tube was sealed and heated at 110° C. for 12 h. The reaction mixture was then cooled to room temperature and the solvent was removed in vacuo. The residue was dissolved in 10 mL ethyl acetate, washed with 1N HCl (2×20 mL) and brine (2×20 mL). The organic layer was then dried (MgSO$_4$) and concentrated at reduced pressure. Purification by flash chormatography (75:25 hexane/ethyl acetate) afforded a crude ester. The crude ester was dissolved in 5 mL of ethanol, 1 mL of 1 N KOH was added and the mixture was stirred at room temperature for 3 h. The reaction was then acidified with 1N HCl and extracted with ethyl acetate (3×5 mL), washed with brine (1×5 mL), dried (MgSO$_4$) and concentrated at reduced pressure. Purification by flash chormatography (50:49:1 hexane/ethyl acetate/acetic acid) afforded the title compound as a light yellow solid (6.7 mg, 11% yield).

$^1$H NMR (CDCl$_3$, 300 MHz) δ 11.33 (bs, 1H), 7.61–8.18 (m, 8H), 7.12 (d, J=8.4 Hz, 1H), 3.99–4.04 (m, 2H), 2.57 (s, 2H), 1.52–1.66 (m, 2H), 1.27–1.44 (m, 18H), 0.86–0.88 (m, 3H).

4-[3-(1-Phenylethyl-4,4-dimethyl-2-oxo-1,2,3,4-tetrahydro-quinolin-6-yl)-3-oxo-propenyl]-benzoic acid (Compound 8e)

Following a procedure similar to that used for the preparation of Compound 8d but using 6-[3-(4-bromophenyl)-acryloyl]-4,4-dimethyl-1-phenylethyl-3,4-dihydro-1H-quinolin-2-one (Intermediate 7e) as the starting material afforded the title compound as a light yellow solid (25% yield).

$^1$H NMR (acetone-d$_6$, 300 MHz) δ 11.29 (bs, 1H), 7.81–8.19 (m, 8H), 7.40 (d, J=8.4 Hz, 1H), 7.32–7.42 (m, 5H), 4.27–4.32 (m, 2H), 2.94–2.99 (m, 2H), 2.53 (s, 2H), 1.31 (s, 6H).

4-[3-(1-Methyl-4,4-dimethyl-2-oxo-1,2,3,4-tetrahydro-quinolin-6-yl)-3-oxo-propenyl]-benzoic acid (Compound 8f)

Following a procedure similar to that used for the preparation of Compound 8d but using 6-[3-(4-bromophenyl)-acryloyl]-4,4-dimethyl-1-methyl-3,4-dihydro-1H-quinolin-2-one (Intermediate 7f) as the starting material afforded the title compound as a light yellow solid (20% yield).

$^1$H NMR (acetone-d$_6$, 300 MHz) δ 11.25 (bs, 1H), 7.68–8.06 (m, 8H), 7.15 (d, J=8.1 Hz, 1H), 3.29 (s, 3H), 2.42 (s, 2H), 1.24 (s, 6H).

BIOLOGICAL ACTIVITY, MODES OF ADMINISTRATION

The compounds of the present invention have anti-tumor activity, as demonstrated by their ability to significantly surpress the growth of breast cancer and prostrate cancer cell lines in tissue cultures. Specifically, the following assay procedure was employed to test certain exemplary compounds of the invention in the breast cancer cell line known in the art as MCF-7 and in the prostate cancer cell line known in the art as LNCaP.

Colony Assay Protocol:
Set 4 mL cultures in 60 mm petri dishes
(medium for LNCaP—RPMI160040 with ITS & linoleic acid)
(medium for MCF-7—DMEN with L-glutamine & without glucose)
Seeding density: LNCaP serum-free 1200 cells/dish; MCF-7 serum-free 1400 cells/dish
Add compound immediately after setting cultures and then change the media and re-feed with compound at day 2 (or day 3 for assays set on Fridays).
Incubated for 14 days (serum free lines)
Fixation and staining:
1. discard used media
2. fix with 10% formal saline for ~30 mins
3. remove formal saline and wash with 2–3 mLs PBS
4. stain with 1% methylene blue in PBS, leave this on for ~1 hr
5. remove stain and wash off in tap water
6. dry overnight and count the colonies The results obtained in these assays are shown in Table 1, expressed in EC$_{50}$ numbers, where EC$_{50}$ is the concentration (expressed as nanomolar) of the compound that results in 50% inhibition of the growth of the cells.

TABLE 1

Clonogenic Assay (Serum-free)

| Compound | EC$_{50}$ for Breast Cancer Cell Line (MCF-7) | EC$_{50}$ for Prostate Cancer Cell Line (LNCaP) |
| --- | --- | --- |
| Compound 8a | 9 nM | 90 nM |
| Compound 8b | 9 nM | 155 nM |
| Compound 8c | 30 nM | 52 nM |
| Compound 8d | 3 nM | 155 nM |
| Compound 8e | 9 nM | Not Active |
| Compound 8f | Not Active | Not Active |

It is generally recognized in the art that inhibitory activity of a compound in tissue culture cancer cell lines is indicative of the ability of the compound to beneficially treat malignancies in tumor bearing mammals, including humans.

The inhibitory activity of the compounds of the invention in the tumor cell lines is unexpected and surprising in view of the fact that compounds where the R$_3$ group of Formula 1 represents a shorter chain, such as Compound 8f are inactive in these assays. Compound 8f is not within the scope of the invention, nor within the scope of Formula 1.

Thus the utility of the compounds of the invention is in the treatment of premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias.

The compounds of the invention may be administered systemically or topically, depending on such considerations as the condition to be treated, need for site-specific treatment, quantity of drug to be administered, and numerous other considerations. For topical administration, when topical administration is considered appropriate, any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form.

For the treatment of malignancies it is likely that the compound of the invention is to be administered systemically. It may be confected as a powder, pill, tablet or the like, or as a syrup or elixir suitable for oral administration. For intravenous or intraperitoneal administration, the compound will be prepared as a solution or suspension capable of being administered by injection. In certain cases, it may be useful to formulate these compounds in suppository form or as extended release formulation for deposit under the skin or intramuscular injection.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of malignancies or premalignancies systemically, an amount between 8 and 160 mg per kg of body weight per day would be administered and would be expected to effect a therapeutic result. More preferably the effective daily dose is likely to be between 25 to 50 mg per kg body weight of the mammal.

What is claimed is:

1. A compound of the formula

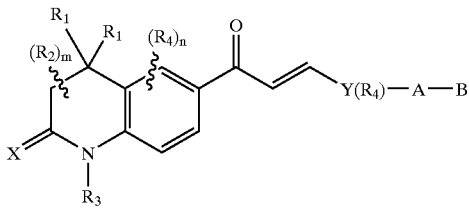

where X is O or S;
  m is an integer having the values of 0 to 2;
  n is an integer having the values of 0 to 3;
  $R_1$ is independently H, or alkyl of 1 to 6 carbons;
  $R_2$ is independently H, alkyl of 1 to 6 carbons, F, Cl, Br or I;
  $R_3$ is alkyl of 5 to 11 carbons, alkenyl of 5 to 11 carbons and having one or two double bonds, alkynyl of 5 to 11 carbons and having one to two triple bonds, alkenylalkynyl having 5 to 11 carbons and one double and one triple bond, or
  $R_3$ is $(CH_2)_r$-phenyl-$(CH_2)_s$—$(CH_3)_t$ where r is an integer having the values of 0 to 7, s is an integer having the values of 0 to 6, and t is an integer having the values of 0 to 1, with the provisos that the sum of r, s and t is in the range of 1 to 7, the phenyl group is 1,3 (meta) or 1,4 (para) substituted with the $(CH_2)_r$ and $(CH_2)_s$—$(CH_3)_t$ groups, the phenyl group optionally being further substituted with one or two $R_4$ groups
  $R_4$ is independently H, alkyl of 1 to 6 carbons, F, Cl, Br or I, alkoxy of 1 to 3 carbons, thioalkoxy of 1 to 3 carbons; $NO_2$, amino, alkylamino or dialkylamino where the alkyl group has 1 to 3 carbons;
  Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_4$ groups;
  A is $(CH_2)_q$ where q is 0–5, branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and
  B is COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-$C_{1-6}$ alkylsilyl, where $R_7$ is an alkyl, cycloalkyl or alkenyl group containing 1 to 5 carbons, $R_8$ is an alkyl group of 1 to 10 carbons, $OCH_2O_{C-1-3}$ alkyl or $OCH_2OCO_{C-1-3}$ alkyl, or trimethylsilylalkyl where the alkyl group has 1 to 10 carbons, or a cycloalkyl group of 5 to 10 carbons, or $R_8$ is phenyl or $C_{1-6}$ alkylphenyl, $R_9$ and $R_{10}$ independently are hydrogen, an alkyl group of 1 to 10 carbons, or a cycloalkyl group of 5–10 carbons, or phenyl or $C_{1-6}$ alkylphenyl, $R_{11}$ is $C_{1-6}$ alkyl, phenyl or $C_{1-6}$ alkylphenyl, $R_{12}$ is $C_{1-6}$ alkyl, and $R_{13}$ is divalent alkyl radical of 2–5 carbons, or a pharmaceutically acceptable salt of said compound.

2. A compound in accordance with claim 1 where Y is phenyl.

3. A compound in accordance with claim 2 where the phenyl group is 1,4-substituted.

4. A compound in accordance with claim 1 where Y is pyridyl.

5. A compound in accordance with claim 4 where the pyridyl group is 1,5-substituted.

6. A compound in accordance with claim 1 where X is O.

7. A compound in accordance with claim 1 where X is S.

8. A compound in accordance with claim 1 where $R_3$ is alkyl of 5 to 11 carbons or phenylethyl.

9. A compound in accordance with claim 1 where the A—B group represents $(CH_2)_q$—COOH, $(CH_2)_q$—$COOR_8$, or $(CH_2)_q$—$CONR_9R_{10}$.

10. A compound in accordance with claim 9 where q is 0.

11. A compound of the formula

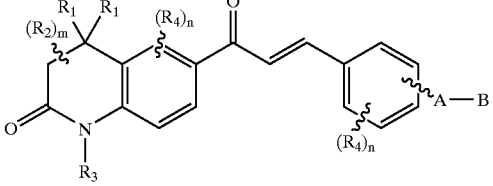

where m is an integer having the values of 0 to 2;
  n is an integer having the values of 0 to 3;
  $R_1$ is independently H, or alkyl of 1 to 6 carbons;
  $R_2$ is independently H, alkyl of 1 to 6 carbons, F, Cl, Br or I;
  $R_3$ is alkyl of 5 to 11 carbons, alkenyl of 5 to 11 carbons and having one or two double bonds, alkynyl of 5 to 11 carbons and having one to two triple bonds, alkenylalkynyl having 5 to 11 carbons and one double and one triple bond, or
  $R_3$ is $(CH_2)_r$-phenyl-$(CH_2)_s$—$(CH_3)_t$ where r is an integer having the values of 0 to 7, s is an integer having the values of 0 to 6, and t is an integer having the values of 0 to 1, with the provisos that the sun of r, s and t is in the range of 1 to 7, the phenyl group is 1,3 (meta) or 1,4 (para) substituted with the $(CH_2)_r$ and $(CH_2)_s$—$(CH_3)_t$ groups, the phenyl group optionally being further substituted with one or two $R_4$ groups
  $R_4$ is independently H, alkyl of 1 to 6 carbons, F, Cl, Br or I, alkoxy of 1 to 3 carbons, thioalkoxy of 1 to 3 carbons; $NO_2$, amino, alkylamino or dialkylamino where the alkyl group has 1 to 3 carbons;
  A is $(CH_2)_q$ where q is 0–5, branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and
  B is COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-$C_{1-6}$ alkylsilyl, where $R_7$ is an alkyl, cycloalkyl or alkenyl group containing 1 to 5 carbons, $R_8$ is an alkyl group of 1 to 10 carbons, $OCH_2O_{C\text{-}1\text{-}3}$ alkyl or $OCH_2OCO_{C\text{-}1\text{-}3}$ alkyl, or trimethylsilylalkyl where the alkyl group has 1 to 10 carbons, or a cycloalkyl group of 5 to 10 carbons, or $R_8$ is phenyl or $C_{1\text{-}6}$ alkylphenyl, $R_9$ and $R_{10}$ independently are hydrogen, an alkyl group of 1 to 10 carbons, or a cycloalkyl group of 5–10 carbons, or phenyl or $C_{1\text{-}6}$ alkylphenyl, $R_1$ is $C_{1\text{-}6}$ alkyl, phenyl or $C_{1\text{-}6}$ alkylphenyl, $R_{12}$ is $C_{1\text{-}6}$ alkyl, and $R_{13}$ is divalent alkyl radical of 2–5 carbons, or a pharmaceutically acceptable salt of said compound.

12. A compound in accordance with claim 11 where $R_1$ is methyl.

13. A compound in accordance with claim 11 where $R_3$ is alkyl of 6 to 9 carbons or phenylethyl.

14. A compound in accordance with claim 11 where m is 0.

15. A compound in accordance with claim 11 where n is 0.

16. A compound in accordance with claim 11 where the A—B group represents $(CH_2)_q$—COOH, $(CH_2)_q$—COOR$_8$, or $(CH_2)_q$—CONR$_9$R$_{10}$.

17. A compound in accordance with claim 16 where q is 0.

18. A compound of the formula where $R_3$ is alkyl of 6 to 9 carbons, and $R'_8$ is H, alkyl of 1 to 6 carbons, $OCH_2O_{C\text{-}1\text{-}3}$ alkyl or $OCH_2OCO_{C\text{-}1\text{-}3}$ alkyl, or a pharmaceutically acceptable salt of said compound.

19. A compound in accordance with claim 18 where $R_3$ is n-hexyl.

20. A compound in accordance with claim 19 where $R'_8$ is H, or a pharmaceutically acceptable salt of said compound.

21. A compound in accordance with claim 18 where $R_3$ is n-heptyl.

22. A compound in accordance with claim 21 where $R'_8$ is H, or a pharmaceutically acceptable salt of said compound.

23. A compound in accordance with claim 18 where $R_3$ is n-octyl.

24. A compound in accordance with claim 23 where $R'_8$ is H, or a pharmaceutically acceptable salt of said compound.

25. A compound in accordance with claim 18 where $R_3$ is n-nonyl.

26. A compound in accordance with claim 25 where $R'_8$ is H, or a pharmaceutically acceptable salt of said compound.

27. A compound in accordance with claim 18 where $R_3$ is phenylethyl.

28. A compound in accordance with claim 27 where $R'_8$ is H, or a pharmaceutically acceptable salt of said compound.

29. A method of treating a mammal afflicted with a malignant or premalignant condition selected from the group consisting of breast cancer and prostrate cancer with a composition comprising a therapeutically effective dose of a compound of the formula where X is O or S;

m is an integer having the values of 0 to 2;

n is an integer having the values of 0 to 3;

$R_1$ is independently H, or alkyl of 1 to 6 carbons;

$R_2$ is independently H, alkyl of 1 to 6 carbons, F, Cl, Br or I;

$R_3$ is alkyl of 5 to 11 carbons, alkenyl of 5 to 11 carbons and having one or two double bonds, alkynyl of 5 to 11 carbons and having one to two triple bonds, alkenylalkynyl having 5 to 11 carbons and one double and one triple bond, or $R_3$ is $(CH_2)_r$-phenyl-$(CH_2)_s$—$(CH_3)_t$ where r is an integer having the values of 0 to 7, s is an integer having the values of 0 to 6, and t is an integer having the values of 0 to 1, with the provisos that the sum of r, s and t is in the range of 1 to 7, the phenyl group is 1,3 (meta) or 1,4 (para) substituted with the $(CH_2)_r$ and $(CH_2)_s$—$(CH_3)_t$ groups, the phenyl group optionally being further substituted with one or two $R_4$ groups $R_4$ is independently H, alkyl of 1 to 6 carbons, F, Cl, Br or I, alkoxy of 1 to 3 carbons, thioalkoxy of 1 to 3 carbons; $NO_2$, amino, alkylamino or dialkylamino where the alkyl group has 1 to 3 carbons;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_4$ groups;

A is $(CH_2)_q$ where q is 0–5, branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is COOH, COOR$_8$, CONR$_9$R$_{10}$, —$CH_2OH$, $CH_2OR_{11}$, $CH_2OCOR_{11}$, CHO, $CH(OR_{12})_2$, CHOR$_{13}$O, —COR$_7$, CR$_7$(OR$_2$)$_2$, CR$_7$OR$_{13}$O, or tri-$C_{1\text{-}6}$ alkylsilyl, where $R_7$ is an alkyl, cycloalkyl or alkenyl group containing 1 to 5 carbons, $R_8$ is an alkyl group of 1 to 10 carbons, $OCH_2O_{C\text{-}1\text{-}3}$ alkyl or $OCH_2CO_{C\text{-}1\text{-}3}$ alkyl, or trimethylsilylalkyl where the alkyl group has 1 to 10 carbons, or a cycloalkyl group of 5 to 10 carbons, or $R_8$ is phenyl or $C_{1\text{-}6}$ alkylphenyl, $R_9$ and $R_{10}$ independently are hydrogen, an alkyl group of 1 to 10 carbons, or a cycloalkyl group of 5–10 carbons, or phenyl or $C_{1\text{-}6}$ alkylphenyl, $R_{11}$ is $C_{1\text{-}6}$ alkyl, phenyl or $C_{1\text{-}6}$ alkylphenyl, $R_{12}$ is $C_{1\text{-}6}$ alkyl, and $R_{13}$ is divalent alkyl radical of 2–5 carbons, or a pharmaceutically acceptable salt of said compound.

30. A method in accordance with claim 29 where the condition is breast cancer.

31. A method in accordance with claim 29 where the condition is prostrate cancer.

* * * * *

UNITED STATES PATENT AND TRADEMARK OFFICE
CERTIFICATE OF CORRECTION

PATENT NO. : 6,683,092 B1
DATED : January 27, 2004
INVENTOR(S) : Tsang et al.

It is certified that error appears in the above-identified patent and that said Letters Patent is hereby corrected as shown below:

<u>Column 17,</u>
Line 8, "$R_1$" is corrected to read -- $R_{11}$ --

Signed and Sealed this

Sixteenth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,683,092 B1
DATED : January 27, 2004
INVENTOR(S) : Tsang et al.

It is certified that error appears in the above-identified patent and that said Letters Patent is hereby corrected as shown below:

Column 9,
Line 17, "Amide" should be -- amide --

Column 12,
Line 37, "$^1$H NM" should be -- $^1$H NMR --

Column 14,
Line 55, "Pa." should be -- Pennsylvania --

Column 18,
Line 49, "$CR_7(OR_2)_2$" should be -- $CR_7(OR_{12})_2$ --

Signed and Sealed this

Fourteenth Day of December, 2004

JON W. DUDAS
*Director of the United States Patent and Trademark Office*